United States Patent
Hu et al.

(10) Patent No.: US 11,629,236 B2
(45) Date of Patent: Apr. 18, 2023

(54) PREPARATION METHOD AND USE OF CROSSLINKED HYDROGEL FOR MUSCLE STEM CELL CULTURE

(71) Applicant: Jiangnan University, Wuxi (CN)

(72) Inventors: Jing Hu, Wuxi (CN); Jian Yin, Wuxi (CN); Xiang Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/846,269

(22) Filed: Jun. 22, 2022

(65) Prior Publication Data

US 2022/0315711 A1    Oct. 6, 2022

Related U.S. Application Data

(63) Continuation of application No. PCT/CN2021/139532, filed on Dec. 20, 2021.

(30) Foreign Application Priority Data

Dec. 30, 2020  (CN) .......................... 202011598284.0

(51) Int. Cl.
  *C08J 3/075*  (2006.01)
  *C08J 3/24*   (2006.01)
  *C12N 5/077*  (2010.01)

(52) U.S. Cl.
  CPC .............. *C08J 3/075* (2013.01); *C08J 3/24* (2013.01); *C12N 5/0659* (2013.01);
  (Continued)

(58) Field of Classification Search
  CPC .......... C08J 3/075; C08J 3/24; C08J 2305/08; C08J 2405/02; C08J 2405/04;
  (Continued)

(56) References Cited

U.S. PATENT DOCUMENTS

2012/0272347 A1   10/2012   Zhang et al.
2019/0264251 A1    8/2019   Cha

FOREIGN PATENT DOCUMENTS

| CN | 101632841 A | 1/2010 |
| CN | 102250390 A | 11/2011 |

(Continued)

OTHER PUBLICATIONS

Tang et. al. ("Construction of physically crosslinked chitosan/sodium alginate/calcium ion double-network hydrogel and its application to heavy metal ions removal" Chem Engineering J. 393, p. 124728, Mar. 14, 2020) (Year: 2020).*

Li-Jih Lin et. al. "A novel dual-structure, self-healable, polysaccharide based hybrid nanogel for biomedical uses" Soft Matter, 2011, 7, p. 5816.

Yan Yan et. al. "Construction of injectable double-network hydrogels for cell delivery" Biomacromolecules, May 30, 2017, vol. 7, Issue 18, p. 2128-2138.

(Continued)

*Primary Examiner* — Robert S Jones, Jr.
*Assistant Examiner* — Jiangtian Xu
(74) *Attorney, Agent, or Firm* — IPro, PLLC; Na Xu

(57) ABSTRACT

The present disclosure discloses a preparation method and use of a crosslinked hydrogel for muscle stem cell culture, and belongs to the technical field of biological food materials. Chitosan, alginate, dextran and $Ca^{2+}$ are crosslinked through physical crosslinking to form a double-network hydrogel with a high mechanical strength, the hydrogel is coated with heparin and collagen through dip coating, such that the hydrogel can immobilize growth factors and adhere to cells. Meanwhile, extracted primary muscle stem cells are inoculated onto the hydrogel and cultured in a growth medium (79% of DMEM, 10% of FBS and 1% of double antibodies) for 24 h. The cells are cultured in an incubator with a differential medium (97% of DMEM, 2% of horse (Continued)

serum and 1% of double antibodies) for 7 d. The hydrogel can enhance the absorption to nutrient substances by the muscle stem cells and facilitate growth of the muscle stem cells. The double-network hydrogel has the potential to be a scaffold for growth of muscle stem cells for cultured meat from stem cells.

6 Claims, 3 Drawing Sheets

(52) U.S. Cl.
CPC ........ *C08J 2305/08* (2013.01); *C08J 2405/02* (2013.01); *C08J 2405/04* (2013.01); *C08J 2405/10* (2013.01); *C12N 2533/54* (2013.01); *C12N 2533/72* (2013.01); *C12N 2533/74* (2013.01); *C12N 2537/10* (2013.01)

(58) Field of Classification Search
CPC ............... C08J 2405/10; C12N 5/0659; C12N 2533/54; C12N 2533/72; C12N 2533/74; C12N 2537/10
See application file for complete search history.

(56) References Cited

FOREIGN PATENT DOCUMENTS

| CN | 104725660 A | | 6/2015 | |
|---|---|---|---|---|
| CN | 107537064 A | | 1/2018 | |
| CN | 109503863 A | * | 3/2019 | ............. A61K 35/28 |
| CN | 109503863 A | | 3/2019 | |
| CN | 110302427 A | | 10/2019 | |
| CN | 112778543 A | | 5/2021 | |
| JP | 2007215519 A | | 8/2007 | |

OTHER PUBLICATIONS

Shuxian Tang et. al. "Construction of physically crosslinked chitosan/sodium alginate/calcium ion double-network hydrogel and its application to heavy metal ions removal" Chem Engineering J. 393, p. 124728, Mar. 14, 2020.

Zhi Li et. al. "Double crosslinking hydrogel with tunable properties for potential biomedical application" J. polymer Research (Aug. 11, 2020) 27:262.

* cited by examiner

PREPARATION METHOD AND USE OF CROSSLINKED HYDROGEL FOR MUSCLE STEM CELL CULTURE

TECHNICAL FIELD

The present disclosure relates a preparation method and use of a crosslinked hydrogel for muscle stem cell culture, particularly to a preparation method and use of a novel double-network physically crosslinked hydrogel, and belongs to the technical field of biological food materials.

BACKGROUND

Cultured meat from stem cells has the potential to reduce the impact of meat products on environment compared with production of traditional meat (Environmental Science & Technology, 2015, 49, 11941-11949). The cultured meat from stem cells has attracted increasing interest and various methods for producing meat from stem cells for food have been proposed (Journal of Integrative Agriculture, 2015, 14, 222-233). However, lacking of an extensible cell culture substrate (scaffold) has become a major challenge limiting the cultured meat from stem cells.

An artificial extracellular matrix (ECM) hydrogel reproduces ECM characteristics in vivo, has mechanical and biochemical properties and thus is a promising material for tissue engineering and 3D cell culture (Nature Biotechnology, 2005, 23, 47-55). Hydrogels can be prepared from synthetic or natural polymers. Natural hydrogels have many unique properties, such as high porosity, high water retention, and tissue-like physical properties that mimic ECM (Gels, 2017, 3, 6-20). Compared with synthetic hydrogels, the natural hydrogels have higher intrinsic biocompatibility and desirable biodegradability (Journal of Materials Science Materials in Medicine, 2019, 30, 115-124). However, the natural hydrogels have certain limitations in specific applications due to poor mechanical strength or the property of too easily degraded.

Currently, the hydrogels are mainly chemically and physically crosslinked. Chemical crosslinking includes: graft copolymerization, free radical polymerization, click chemistry, enzymatic reaction, thermal gelation, and radiation crosslinking which are mostly accomplished by chemical reagents. Physical crosslinking is accomplished by intermolecular interactions (ionic crosslinking, hydrophobic interaction and hydrogen bonding). Obviously, the physical crosslinking is more convenient and environment-friendly, and has better biocompatibility. However, the physical crosslinking has disadvantages that a crosslinking strength is weak and the formed hydrogels are easy to collapse. Therefore, it is imperative to construct the physically crosslinked natural hydrogels that have higher mechanical property and are less prone to collapse.

Alginate is linear polysaccharide extracted from brown algae, which is a natural anionic polymer electrolyte, and consists of two monosaccharides α-L-guluronic acid (G) and 6-D-mannuronic acid (M) (Biomaterials, 1999, 20, 45-53). The alginate is widely available and inexpensive, and has various excellent characteristics such as biocompatibility. When interacting with divalent ions such as $Ca^{2+}$, $Sr^{2+}$ and $Ba^{2+}$, the alginate becomes a dense three-dimensional structure to improve the mechanical property. The degradation rate of an alginate hydrogel is difficult to control since the stability is a considerable challenge for ionic polymers. Therefore, the alginate has the main disadvantages of poor mechanical property and poor cell adhesion.

Chitosan is extracted from shrimps, crabs and insects and is a natural linear compound consisting of 6-(1,4) glycosidic bond linked glucosamine and N-acetylglucosamine. Unlike other natural polysaccharides, chitosan is the only basic polysaccharide and cationic polymer electrolyte, prone to form oxides, and capable of chelating metal ions and forming films. The chitosan is recognized as a food additive by the U.S. Food and Drug Administration (FDA) because it is non-toxic, environmentally friendly and biodegradable (Journal of Polymers and the Environment, 2016, 25, 973-982). In addition, the chitosan has been widely used in biomedical fields such as drug administration, tissue engineering and cancer diagnosis (European Polymer Journal, 2013, 49, 780-792) due to its biocompatibility and mechanical property matching with natural ECM (Carbohydrate Polymer, 2010, 82, 227-232). Nevertheless, the chitosan is only soluble in water at a pH value less than 6.2 and requires a balance between hydrogen bonding, hydrophobic interaction and interchain electrostatic interaction to form a gel.

It is obvious that the negative ion alginate and the positive ion chitosan can be mutually attracted by electrostatic attraction to form a hydrogel. This form of hydrogel is biocompatible and more environmentally friendly, but has major shortcomings of poor mechanical property and poor cell adhesion. Thus, it is still a challenge to obtain a natural hydrogel with high biocompatibility, high crosslinking strength and strong cell adhesion.

SUMMARY

Technical Problems

In order to prepare a natural hydrogel with high biocompatibility, high crosslinking strength and strong cell adhesion, the present disclosure provides a novel double-network physically crosslinked hydrogel for culturing stem cells with strong adsorption force and not easy to collapse.

Technical Solutions

The present disclosure prepares a chitosan/dextran/alginate/calcium ion double-network physically crosslinked hydrogel by combining a semi-dissolving acidified sol-gel transition method with an internal gel method, then dip-coating heparin to enhance the ability of the hydrogel to adsorb proteins and growth factors, and then coating with collagen by the protein-adsorbing ability of the heparin. These modifying groups enable the hydrogel to adhere to cells and release growth factors in a controlled manner. Besides, after a large amount of water swelling, the double-network crosslinked structure enables the hydrogel to have enhanced mechanical property and maintain integrity through a synergistic effect of the two networks. At the same time, the hydrogel solves the problem of cytotoxicity caused by toxic chemical crosslinking agents used in a chemically crosslinked network.

The present disclosure provides a preparation method of a crosslinked hydrogel for muscle stem cell culture, including: dissolving sodium alginate to obtain a solution and adding a certain amount of calcium carbonate into the sodium alginate solution until the calcium carbonate is uniformly dispersed to obtain a slurry; dissolving dextran to obtain a solution and adding chitosan into the dextran solution until the chitosan is uniformly dispersed to obtain a slurry; mixing the two slurries, pouring the mixed slurry into a mold, putting the mold into a sealed container filled with hydrochloric acid, and crosslinking to obtain a double-network physically crosslinked hydrogel; and dipping into a heparin sodium solution to obtain a heparin-coated hydrogel and then dipping into a collagen solution to obtain a collagen and heparin-coated double-network crosslinked hydrogel.

Preferably, the method includes the following steps:

(1) preparing a first gel material: uniformly mixing and dissolving the sodium alginate (Alg) in water to obtain the sodium alginate solution, adding the certain amount of calcium carbonate into the sodium alginate solution, and stirring until the calcium carbonate is uniformly dispersed to obtain the first gel material;

(2) preparing a second gel material: mixing and dissolving the dextran (Dex) in water to obtain the dextran solution, adding the chitosan (CS) to the dextran solution, and stirring until the chitosan is uniformly dispersed to obtain the second gel material;

(3) preparing a chitosan/dextran/alginate/calcium ion double-network crosslinked hydrogel: uniformly mixing the first gel material and the second gel material, pouring an obtained mixture into the mold, putting the mold into the sealed container filled with hydrochloric acid, and sealing the slurry using the hydrochloric acid for 12-36 h to obtain a double-network crosslinked CS/Dex/Alg/$Ca^{2+}$ hydrogel;

(4) dip-coating heparin: dipping the hydrogel prepared in step (3) in the heparin sodium solution for 15-45 min to obtain a heparin-coated CS/Dex/Alg/$Ca^{2+}$ hydrogel; and (5) dip-coating collagen: dipping the heparin-coated CS/Dex/Alg/$Ca^{2+}$ hydrogel obtained in step (4) in the collagen solution for 15-45 min to obtain a collagen and heparin-coated CS/Dex/Alg/$Ca^{2+}$ hydrogel and freeze-drying the hydrogel.

Preferably, the water in the method is deionized water or high purity water.

Preferably, the alginate in step (1) is a linear polysaccharide extracted from brown algae, which is a natural anionic polymer electrolyte consisting of two monosaccharides α-L-guluronic acid (G) and 6-D-mannuronic acid (M), where the α-L-guluronic acid (G) and the 6-D-mannuronic acid (M) in the sodium alginate have a ratio of 70/30 to 30/70.

Preferably, in step (1), the content of the sodium alginate in the sodium alginate solution is 1-2 wt %.

Preferably, in step (1), the content of the $CaCO_3$ in the first gel material is 0.01-0.5 wt %.

Preferably, in step (1), the calcium carbonate is stirred for 6-12 h.

Preferably, in step (2), the dextran may have a molecular weight of 80-100 kDa.

Preferably, in step (2), the content of the dextran in the dextran solution is 0.5-2.0 wt %.

Preferably, in step (2), the chitosan in the second gel material have a deacetylation degree of 90-95% and a molecular weight of 50-250 kDa.

Preferably, in step (2), the content of the chitosan in the second gel material is 0.5-3 wt %.

Preferably, in step (3), the first gel material and the second gel material are mixed at a mass ratio of 1:1 to 2:1.

Preferably, in step (3), the mold is a cuboid (with a length of 50-200 mm, a width of 50-200 mm and a height of 10-50 mm), where there are multiple capillary structures in the middle of the cuboid (with a diameter of 0.3-0.6 mm), thus the hydrogel has a shape of long muscle fibers parallel to each other.

Preferably, in step (3), the hydrochloric acid solution hss a concentration of 5-10 mol/L.

Preferably, in step (4), the heparin solution has a concentration of 1-7 g/L.

Preferably, in step (4), dip-coating heparin specifically includes: soaking the prepared CS/Dex/Alg/$Ca^{2+}$ hydrogel in PBS for 15-45 min, dipping in the heparin solution for 15-45 min 3-5 times and washing with PBS to remove heparin not adsorbed on a surface.

Preferably, in step (5), the collagen solution has a concentration of 10-20 wt %.

Preferably, in step (5), dip-coating collagen specifically includes: soaking the prepared heparin-coated CS/Dex/Alg/$Ca^{2+}$ hydrogel in PBS for 15-45 min, dipping in the collagen solution for 15-45 min 3-5 times and washing with PBS to remove collagen not adsorbed on a surface.

Preferably, in step (5), the freeze-drying is conducted at a temperature of −60° C. to −80° C. for 12-24 h.

The present disclosure provides a crosslinked hydrogel for muscle stem cell culture prepared by the preparation method.

The present disclosure provides a culture medium containing the crosslinked hydrogel for muscle stem cell culture.

The present disclosure provides a method for culturing muscle stem cells, where in the method, the crosslinked hydrogel for muscle stem cell culture is used as a culture medium.

Preferably, the muscle stem cells include but are not limited to porcine muscle stem cells, bovine muscle stem cells, etc.

The present disclosure provides use of the preparation method or the crosslinked hydrogel for muscle stem cell culture in the field of cultured meat.

Beneficial effects of the present disclosure:

1. The present disclosure successfully prepares a double-network physically crosslinked CS/Dex/Alg/$Ca^{2+}$ hydrogel by combining a semi-dissolving acidified sol-gel transition method with an internal gel method, dissolving calcium carbonate and chitosan, and forming a network with sodium alginate and dextran during a dissolving process. The double-network synergistic effect enables the hydrogel to have complete mechanical property, such that the hydrogel is not easily collapsed during a subsequent stem cell culture process. Besides, a strongly crosslinked hydrogel is obtained without using toxic chemical crosslinking agents.

2. The heparin introduced into the hydrogel system in the present disclosure is conducive to immobilize growth factors of stem cells and can release the growth factors in a long term. At the same time, the heparin is introduced to help the hydrogel to crosslink collagen.

3. The collagen is further introduced into the hydrogel system and beneficial to adhering to stem cells and improving the biocompatibility of the hydrogel.

DETAILED DESCRIPTION

Figure 1:
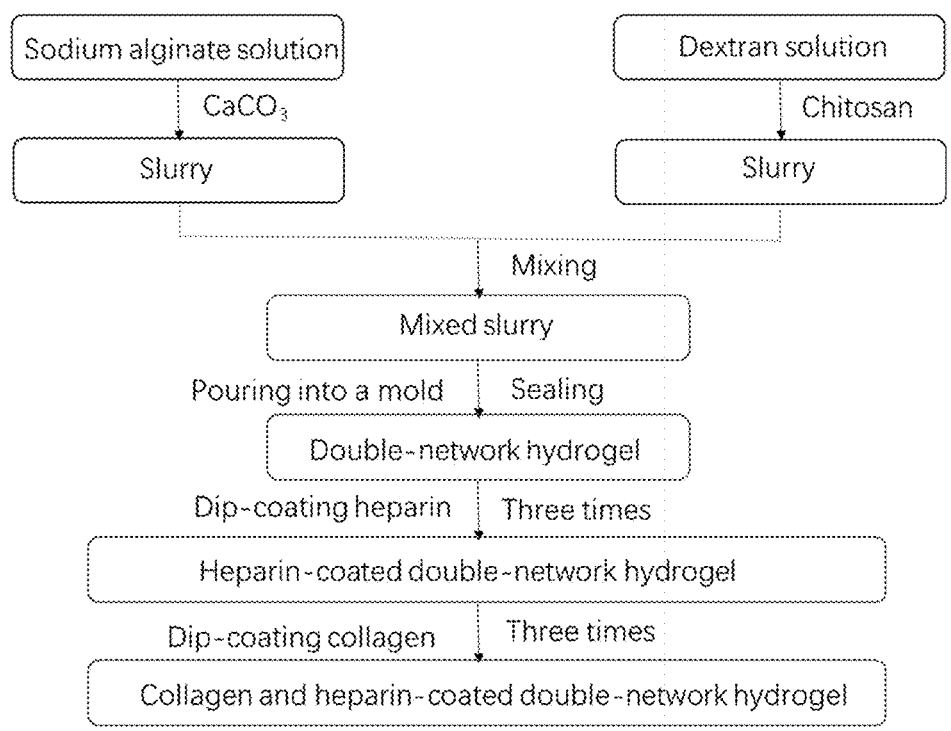
FIG. 1 is a flow chart of preparation of a collagen and heparin-coated CS/Dex/Alg/$Ca^{2+}$ hydrogel.
Figure 2:
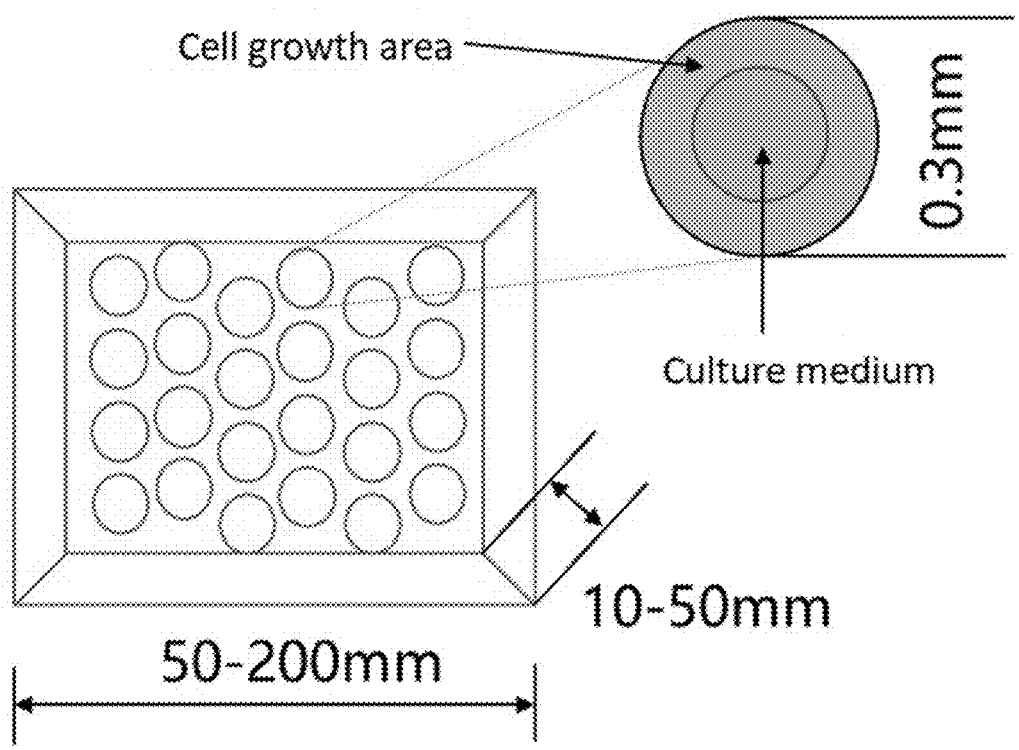
FIG. 2 is a schematic structural diagram of a production mold for multiple-capillary-shaped cultured meat of the present disclosure.
Figure 3A:
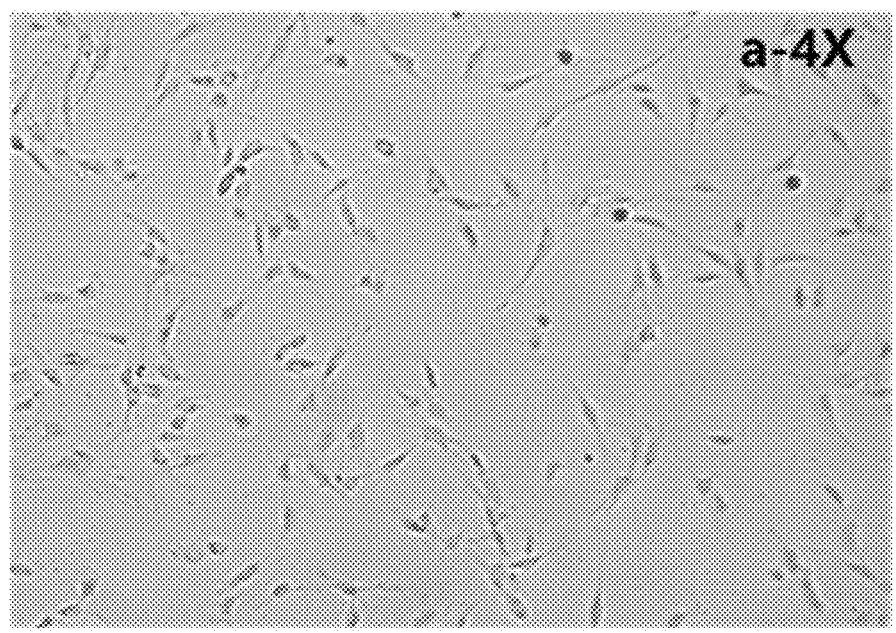
FIG. 3A is a microscopic image (4×) of primary porcine muscle stem cells before differentiation.
Figure 3B:
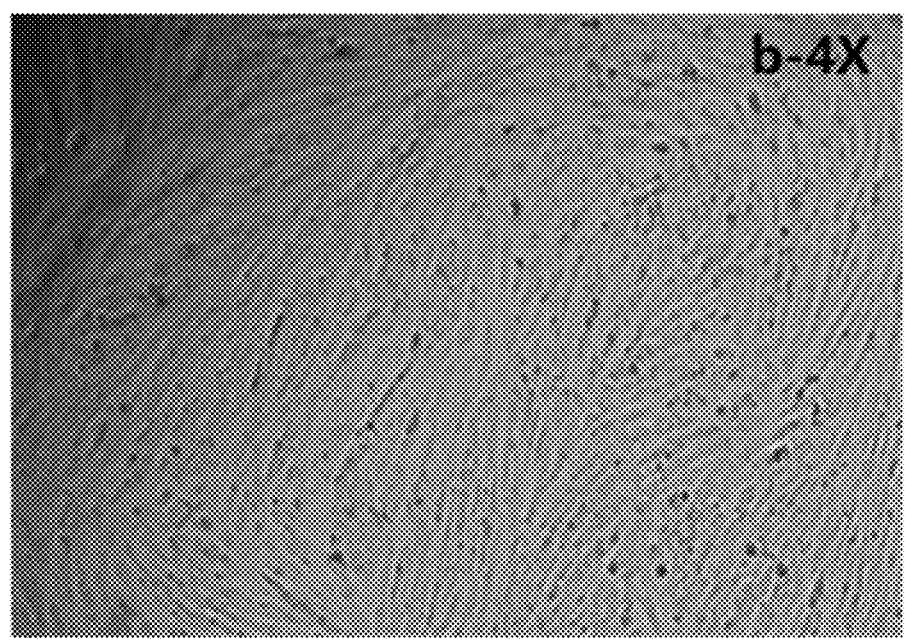
FIG. 3B is a microscopic image (4×) of primary porcine muscle stem cells 72 h after differentiation.

Embodiments of the present disclosure will be described in detail below with reference to examples, but those skilled in the art will understand that the following examples are only used to illustrate the disclosure and should not be regarded as limiting the scope of the disclosure. If no specific conditions are specified in the examples, the examples will be conducted according to conventional conditions or the conditions recommended by the manufacturer. All used reagents or instruments for which manufacturers are not specified are conventional commercially-available products.

Example 1

Preparation of Chitosan/Dextran/Alginate/Calcium Ion Double-Network Crosslinked Hydrogel 1 g of sodium alginate (AR; 120 kDa; G/M ratio of 35/65) and 99 mL of deionized water were added to a beaker while stirring until the sodium alginate was dissolved to obtain a sodium alginate solution with a concentration of 1 wt %, then 0.1 g of calcium carbonate was added to the sodium alginate solution and stirred until the calcium carbonate was uniformly dispersed to form a first gel material similar to a slurry. 1 g of dextran (AR; 80-100 kDa) and 99 mL of deionized water were added to a beaker and stirred until the dextran was dissolved to obtain a dextran solution with a concentration of 1 wt %, 2 g of chitosan (a deacetylation degree of 90.24%; 230 kDa) was added to the dextran solution and stirred until the chitosan was evenly dispersed to form a second gel material similar to a slurry. The two gel materials were mixed and stirred uniformly at a ratio of the first gel material to the second gel material of 1:1. The mixed slurry was poured into a mold, the mold was placed in a sealed plastic box filled with 100 mL of hydrochloric acid (1 mol/L), and the slurry was subjected to sol-gel transition for 24 h. A prepared hydrogel was demolded and rinsed with deionized water.

Example 2

Heparin-Coated Chitosan/Dextran/Alginate/Calcium Ion Double-Network Crosslinked Hydrogel Heparin sodium (0.5 g) and deionized water (100 mL) were added to a beaker to obtain a heparin solution (5.0 g/L). The prepared CS/Dex/Alg/Ca$^{2+}$ hydrogel was soaked in PBS for 30 min and dipped in the heparin solution for 15 min three times, heparin not adsorbed on a surface was washed away with PBS, and a heparin-coated CS/Dex/Alg/Ca$^{2+}$ hydrogel was obtained by an electrostatic adsorption.

Example 3

Collagen-Coated Chitosan/Dextran/Alginate/Calcium Ion Double-Network Crosslinked Hydrogel Collagen and deionized water were added to a beaker to obtain a collagen solution (20 wt %). The prepared heparin-coated CS/Dex/Alg/Ca$^{2+}$ hydrogel was soaked in PBS for 30 min and dipped in the collagen solution for 15 min three times, collagen on a surface was washed away with PBS, and a collagen and heparin-coated CS/Dex/Alg/Ca$^{2+}$ hydrogel was obtained by an interaction between the collagen and the heparin. Subsequently, the hydrogel was freeze-dried in a vacuum freeze dryer (−80° C.).

Example 4

Adsorption of Growth Factors by Hydrogel

The double-network physically crosslinked hydrogel was washed with PBS, the obtained hydrogel was dipped in 75% ethanol for 20 min and repeatedly dipped in sterile deionized water for 5 min, the ethanol was washed with sterile water three times to remove all residual ethanol (Food Hydrocolloids, 2017, 72, 210-218), the hydrogel was transferred to a solution containing growth factors of vitamin C (0.05 μg/mL) and bFGF (10 ng/mL), and the hydrogel adsorbing the growth factors was obtained after swelling for 24 h. The content of the bFGF (450 nm) and the vitamin C (536 nm) in the remaining solution was detected by an enzyme-linked immunosorbent assay (ELISA), and adsorption of the growth factors by the hydrogel was calculated according to differences between initial concentrations of the bFGF and the vitamin C in the solution and the concentrations in the remaining solution.

Experiment results are as shown in the following Table 1

TABLE 1

| Sample | bFGF (ng/ml) | Vitamin C (μg/mL) |
| --- | --- | --- |
| Example 1 | 5.1 | 0.012 |
| Example 2 | 8.2 | 0.038 |
| Example 3 | 10.0 | 0.050 |

Example 5

Release of Growth Factors by Hydrogel

The hydrogel adsorbing the growth factors in Example 4 was put into 1 mL of sterile PBS solution, the PBS solution in the experiment was collected using a pipette every 24 h, an equal volume of new sterile PBS solution was added, and the solution collected from a well plate was stored in an EP tube and stored and placed in a −20° C. refrigerator for detection. The concentration of the bFGF (450 nm) and the content of the vitamin C (536 nm) in the collected solution were detected by an enzyme-linked immunosorbent assay (ELISA).

According to a growth factor release experiment, the bFGF and the vitamin C adsorbed by the hydrogel in Example 3 were not detectable on the 10th day, the bFGF and the vitamin C adsorbed by the hydrogel in Example 2 were not detectable on the 8th day, and the bFGF and the vitamin C adsorbed by the hydrogel in Example 1 were not detectable on the 4th day. It can be seen that the prepared hydrogel is beneficial to immobilizing growth factors of stem cells and can release the growth factors in a long term.

Example 6

Culture of Porcine Muscle Stem Cells on Double-Network Hydrogel

The hydrogel containing the growth factors obtained in Example 4 was used, and cells were seeded on the prepared double-network hydrogel at a density of 1.500 cells/mm$^2$ and incubated in a growth medium (79% DMEM, 10% FBS, 1% double antibodies, 79% DMEM) for 24 h. The cells are cultured in a differential medium (97% of DMEM, 2% of horse serum and 1% of double antibodies) for 7 d. A large number of significantly proliferating cells were observed in capillary structures after 7 d of culture.

Example 7

Mechanical Testing of Hydrogel

The hydrogel was tested in uniaxial compression using an Instron mechanical test frame (model 5565A). Stress was calculated from a force curve $$\sigma = \frac{F}{A_0},$$

where F is a force used to compress a sample and Ao is an initial area of the sample. Modulus of gel was calculated by $$G(t) = \frac{\sigma(t)}{\gamma}.$$

The sample was tested at least in triplets. Before testing, the hydrogel was carefully examined for cracks or deformation. The hydrogel was aligned in the center of a stainless steel compression plate. The hydrogel was slippery and can expand freely when compressed. The stress relaxation of the sample was investigated under compression of 5%, 10% and 20% strain using an initial crosshead speed of 4% strain/sec. The study found that when the hydrogel prepared by the present disclosure was relaxed, it had a stress response as long as 300 s.

Example 8

Preparation of Scanning Electron Microscopy (SEM) Hydrogel Sample

Morphology of the freeze-dried hydrogel was imaged using a Hitachi S-4800 SEM (Hitachi, Japan) with an accelerating voltage of 5 kV. Before testing, a cross-section of the hydrogel was fixed on a metal substrate with a conductive tape and sputter-coated with gold. The study found that the hydrogel prepared by the present disclosure had a porous structure with various pore sizes and the structure was beneficial to swelling of growth factors and promoted diffusion of the growth factors into the hydrogel. Moreover, the pores had a relatively large specific surface area and were conducive to adhesion of muscle stem cells.

Example 9

Preparation of Heparin and Collagen-Coated Chitosan/Dextran/Alginate/Calcium Ion Double-Network Crosslinked Hydrogel 2 g of sodium alginate (AR; 120 kDa; G/M ratio of 70/30) and 98 mL of deionized water were added to a beaker while stirring until the sodium alginate was dissolved to obtain a sodium alginate solution with a concentration of 2 wt %, 0.3 g of calcium carbonate was added to the sodium alginate solution and stirred until the calcium carbonate was uniformly dispersed to form a first gel material similar to a slurry. 2 g of dextran (AR; 80-100 kDa) and 98 mL of deionized water were added to a beaker and stirred until the dextran was dissolved to obtain a dextran solution with a concentration of 2 wt %, 3 g of chitosan (a deacetylation degree of 90.24%; 230 kDa) was added to the dextran solution and stirred until the chitosan was evenly dispersed to form a second gel material similar to a slurry. The two gel materials were mixed and stirred uniformly at a mass ratio of the first gel material to the second gel material of 2:1. The mixed slurry was poured into a mold, the mold was placed in a sealed plastic box filled with 100 mL of hydrochloric acid (1 mol/L), and the slurry was subjected to sol-gel transition for 12 h. A prepared hydrogel was demolded and rinsed with deionized water. Heparin sodium (0.1 g) and deionized water (100 mL) were added to a beaker to obtain a heparin solution (1.0 g/L). The prepared CS/Dex/Alg/$Ca^{2+}$ hydrogel was soaked in PBS for 15 min and dipped in the heparin solution for 45 min five times, heparin not adsorbed on a surface was washed away with PBS, and a heparin-coated CS/Dex/Alg/$Ca^{2+}$ hydrogel was obtained by an electrostatic adsorption. Collagen and deionized water were added to a beaker to obtain a collagen solution (10 wt %). The prepared heparin-coated CS/Dex/Alg/$Ca^{2+}$ hydrogel was soaked in PBS for 15 min and dipped in the collagen solution for 45 min five times, collagen on a surface was washed away with PBS, and a collagen and heparin-coated CS/Dex/Alg/$Ca^{2+}$ hydrogel was obtained by an interaction between the collagen and the heparin. Subsequently, the hydrogel was freeze-dried in a vacuum freeze dryer (−80° C.). The prepared hydrogel was porous and a large number of porcine muscle stem cells were observed in the capillary structures after the porcine muscle stem cells were cultured on the hydrogel for 7 d.

Comparative Example 1

Only chitosan and sodium alginate were crosslinked, that is, there was no calcium carbonate in the first gel material and no dextran in the second gel material. The remaining steps were the same as those in Examples 1-3 and a hydrogel was prepared.

A growth factor adsorption experiment was conducted on the prepared hydrogel. It was found that when growth factors were adsorbed for 6 h, the hydrogel showed a large amount of collapse with a proportion of 60%. The prepared hydrogel was subjected to stress testing and only had a stress response of 30 s.

Comparative Example 2

Only sodium alginate and $Ca^{2+}$ were used, that is, there was no second gel material. The remaining steps were the same as those in Examples 1-3 and a hydrogel was prepared.

A growth factor adsorption experiment was conducted on the prepared hydrogel. It was found that when growth factors were adsorbed for 12 h, the hydrogel showed a large amount of collapse with a proportion of 55%. The prepared hydrogel was subjected to stress testing and only had a stress response of 80 s.

Comparative Example 3

No dextran was used, that is, the second gel material only contained chitosan. The remaining steps were the same as those in Examples 1-3 and a hydrogel was prepared.

A growth factor adsorption experiment was conducted on the prepared hydrogel. After 24 h of adsorption, the adsorbed bFGF was 10.0 ng/mL and the vitamin C was 0.050 µg/mL. The adsorbed bFGF and vitamin C were not detectable on the 10th day. The prepared hydrogel was subjected to stress testing and had a stress response of 250 s. After a porcine muscle stem cell culture experiment, the amount of adhered cells in the hydrogel was significantly lower than that of in the dextran-containing hydrogel.

Comparative Example 4

After the two gel materials prepared according to Example 1 were mixed, an obtained mixed slurry was poured into a mold, the mold was put into a sealed plastic box filled with 100 mL of PBS (1 mol/L), and subjected to transformation for 24 h. After demolding, it was found that the slurry still existed. The slurry does not possess basic mechanical properties of the hydrogel and stress characteristics, and is not capable of adsorbing and releasing growth factors. Porcine muscle stem cells cannot be cultured on the slurry.

Comparative Example 5

1 g of sodium alginate (AR; 120 kDa; G/M ratio of 35/65) and 49 mL of deionized water were added to a beaker while stirring until the sodium alginate was dissolved to obtain a sodium alginate solution with a concentration of 2 wt %; 0.1 g of calcium chloride and 49 mL of deionized water were added to a beaker while stirring until the calcium chloride was dissolved to obtain a calcium chloride solution with a concentration of 0.2 wt %; 1 g of dextran (AR; 80-100 kDa) and 49 mL of deionized water were added to a beaker and stirred until the dextran was dissolved to obtain a dextran solution with a concentration of 2 wt %; 2 g of chitosan (a deacetylation degree of 90.24%; 230 kDa) and 49 mL of hydrochloric acid (1 mol/L) were added while stirring until the chitosan was dissolved to obtain a chitosan solution with a concentration of 4 wt %; and the sodium alginate solution, the calcium chloride solution, the dextran solution and the chitosan solution were stirred and mixed uniformly at a mass ratio of 1:1:1:1, and standing was conducted for 24 h to obtain a hydrogel. The hydrogel was prepared according to steps of Examples 2 and 3.

The prepared hydrogel was subjected to stress testing and had a stress response of 180 s. After a porcine muscle stem cell culture experiment, the amount of adhered cells in the hydrogel was relatively less and significantly lower than that of the hydrogel prepared by a semi-dissolving acidified sol-gel transition method.

Although the disclosure has been disclosed as above in the preferred examples, it is not intended to limit the disclosure. Any person skilled in the art can make various changes and modifications without departing from the spirit and scope of the disclosure. Therefore, the protection scope of the disclosure should be as defined in the claims.

What is claimed is:

1. A preparation method of a crosslinked hydrogel for muscle stem cell culture, comprising: dissolving sodium alginate to obtain a solution and adding a predetermined amount of calcium carbonate into the sodium alginate solution until the calcium carbonate is uniformly dispersed to obtain a slurry; dissolving dextran to obtain a solution and adding chitosan into the dextran solution until the chitosan is uniformly dispersed to obtain a slurry; mixing the two slurries, pouring the mixed slurry into a mold, putting the mold into a sealed container filled with hydrochloric acid, and crosslinking to obtain a double-network physically crosslinked hydrogel; and dipping into a heparin sodium solution to obtain a heparin-coated hydrogel and then dipping into a collagen solution to obtain a collagen and heparin-coated double-network crosslinked hydrogel.

2. The preparation method of a crosslinked hydrogel for muscle stem cell culture according to claim 1, comprising the following steps:
   (1) preparing a first gel material: uniformly mixing and dissolving the sodium alginate (Alg) in water to obtain the sodium alginate solution, adding the predetermined amount of calcium carbonate ($CaCO_3$) into the sodium alginate solution, and stirring until the calcium carbonate is uniformly dispersed to obtain the first gel material;
   (2) preparing a second gel material: mixing and dissolving the dextran (Dex) in water to obtain the dextran solution, adding the chitosan (CS) to the dextran solution, and stirring until the chitosan is uniformly dispersed to obtain the second gel material;
   (3) preparing a chitosan/dextran/alginate/calcium ion double-network crosslinked hydrogel: uniformly mixing the first gel material and the second gel material, pouring an obtained mixture into the mold, putting the mold into the sealed container filled with hydrochloric acid, and sealing the slurry using the hydrochloric acid for 12-36 hours to obtain a double-network crosslinked CS/Dex/Alg/$Ca^{2+}$ hydrogel;
   (4) dip-coating heparin: dipping the hydrogel prepared in step (3) in the heparin sodium solution for 15-45 min to obtain a heparin-coated CS/Dex/Alg/$Ca^{2+}$ hydrogel; and
   (5) dip-coating collagen: dipping the heparin-coated CS/Dex/Alg/$Ca^{2+}$ hydrogel obtained in step (4) in the collagen solution for 15-45 min to obtain a collagen and heparin-coated CS/Dex/Alg/$Ca^{2+}$ hydrogel and freeze-drying the hydrogel.

3. The preparation method of a crosslinked hydrogel for muscle stem cell culture according to claim 2, wherein in step (1), α-L-guluronic acid (G) and 6-D-mannuronic acid (M) in the sodium alginate has a ratio of 70/30 to 30/70.

4. The preparation method of a crosslinked hydrogel for muscle stem cell culture according to claim 2, wherein in step (1), the content of the sodium alginate in the sodium alginate Alg solution is 1-2 wt % and the content of the $CaCO_3$ in the first gel material is 0.01-0.5 wt %.

5. The preparation method of a crosslinked hydrogel for muscle stem cell culture according to claim 2, wherein the content of the dextran in the dextran solution is 0.5-2.0 wt % and the content of the chitosan in the second gel material is 0.5-3 wt %.

6. The preparation method of a crosslinked hydrogel for muscle stem cell culture according to claim 2, wherein the first gel material and the second gel material are mixed at a mass ratio of 1:1 to 2:1.

* * * * *